Figure 1:
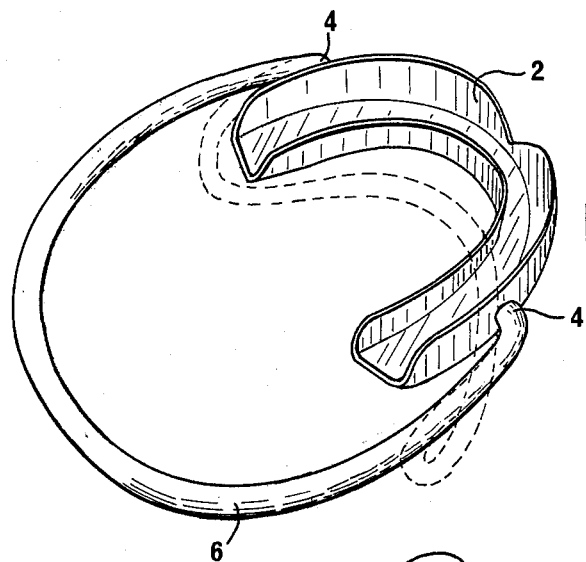

United States Patent [19]

Bruhn et al.

[11] 4,305,709
[45] Dec. 15, 1981

[54] TOOTH PROTECTORS

[75] Inventors: Peter E. Bruhn, Egevej 2, Hou, 8300 Odder, Denmark; Henning B. Jensen, Stouby, Denmark

[73] Assignee: Peter E. Bruhn, Stouby, Denmark

[21] Appl. No.: 138,279

[22] Filed: Apr. 9, 1980

[51] Int. Cl.³ .............................................. A61C 00/00
[52] U.S. Cl. .................................... 433/136; 128/136
[58] Field of Search ................. 433/136, 42, 179, 140, 433/93; 128/12, 13, 14, 15, 136

[56] References Cited

U.S. PATENT DOCUMENTS 3,027,643 4/1962 Cohen .................................... 433/93
3,536,069 10/1970 Gore ..................................... 128/136

Primary Examiner—Robert Peshock
Attorney, Agent, or Firm—Craig and Antonelli

[57] ABSTRACT

A mouthpiece for covering or protecting the upper dentition of patients under medical or surgical treatments involving oral intervention, comprising an arched tray member to be placed on the dentition and a resilient loop member connected with opposed exterior wall portions of the tray member and in its natural position extending rearwardly from the tray member in the general plane of this member. When the loop member is bent downwardly and forwardly against its own resiliency the foremost portion thereof may be placed in the groove between the outside of the lower dentition and the inside of the underlip and lower cheek portions of the patient, whereby the upper tray member will be effectively held in its mounted position with a low degree of discomfort for the patient. The mouthpiece also causes a certain cheek distension for better skin fit of a mask.

5 Claims, 3 Drawing Figures

U.S. Patent  Dec. 15, 1981  4,305,709

TOOTH PROTECTORS

The present invention relates to a mouthpiece for protecting the upper dentition of patients and of the type specified in the introductory clause of claim 1. Such a mouthpiece, when placed to cover the upper dentition of the patient, will serve both to protect the teeth against injuring influence from the medical or surgical implements as used in the oral region of the patient, e.g. by gastroscopy or anaestesia and to protect the patient against loose teeth dropping into the throat of the patient during such work. The use of such a mouthpiece inevitably causes a restriction of the available effective mouth opening, and it is undesirable, therefore, to use a mouthpiece of the well known type as used by sportsmen for protecting both the upper and the lower dentition; for medical purposes it is generally fully sufficient to protect but the upper dentition, and the combined use of an upper and lower dentition protection would result in an undersirable restriction of the effective mouth opening.

These basic conditions leave the medical mouthpiece with a fastening problem which does not exist with the combined upper and lower dentition protectors, because the latter may include resilient means interconnecting the respective upper and lower protector tray elements so as to generally urge these away from each other and thus holding each of them in close contact with the respective dentition no matter how the jaw is moved.

Medical or surgical mouthpieces, therefore, are traditionally made as a single arched tray element to be fastened in a direct manner to the upper dentition, normally by means of some adhesive substance placed inside the tray element, but generally this is no ideal solution, already because the positioning and the subsequent removal of the mouthpiece involve inconveniences for the patient.

It is purpose of this invention to provide a mouthpiece for protecting the upper dentition which is easy both to mount and remove and causes a minimum of inconvenience for the patient.

This purpose is achieved by designing the mouthpiece according to the features stated in the characterizing clause of claim 1. It has been found that the resilient loop member mentioned therein is a perfect means for holding the arched tray member against the upper dentition without causing any restriction of the effective mouth opening. To the contrary, the loop member in its mounted position may serve to distend the cheeks and thus even broaden the effective opening, while the forwardly bent loop portion will be entirely hidden away between the outside of the lower dentition and the inside of the underlip and lower cheek portions of the patient. In this manner the mounted loop member will be effectively prevented from displacing itself in the undermouth of the patient, and it will correspondingly safely hold the tray member on the upper dentition. It is of course also an advantage that the mouthpiece is usable with little inconvenience for the patient and that it is indeed very easy to mount and dismount.

Figure 2:
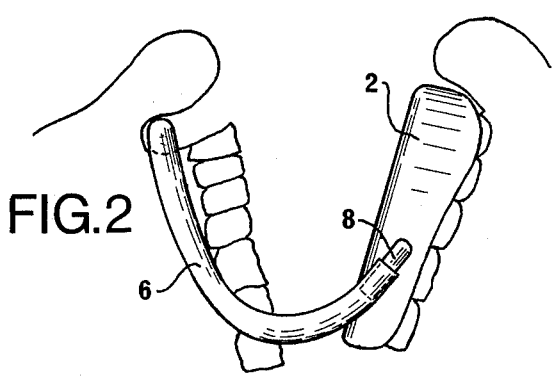
Figure 3:
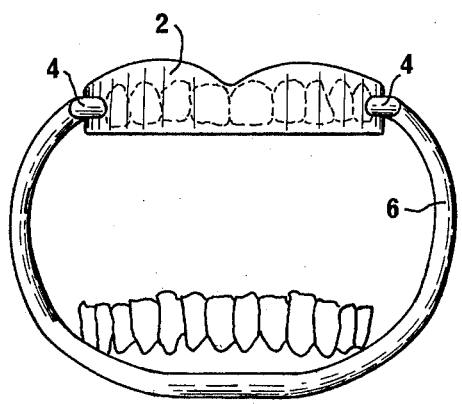

In the following the invention is described in more detail with reference to the accompanying drawing, in which:

FIG. 1 is a perspective view of a mouthpiece according to a preferred embodiment of the invention, FIG. 2 is a schematic side view of the mouthpiece in its mounted position, and FIG. 3 is a schematic front view thereof.

The mouthpiece shown in FIG. 1 is made as a casting of a suitable rubber or artificial material and comprises an arched tray member 2 adapted to the shape of the human upper dentition. Approximately midways between the front and rear end planes of the tray member there is provided on the exterior tray wall an outwardly projecting stub 4, and the two opposed stubs 4 are interconnected by an arched loop member 6 which in FIG. 1 is an integrally formed, solid and resiliently bendable rod element. As shown in dotted lines in FIG. 1 the loop member may be bent downwardly and forwardly generally about a transverse axis, and in this condition it is easily mountable in the mouth of a patient when the tray member is laid against the upper dentition and the forward portion of the bent loop member is placed in the groove between the outside of the lower dentition and the inside of the underlip and lower cheek portions of the patient.

Just behind the stubs 4 the loop member 6 has a rearwardly diverging configuration, and in the mounted position this will give rise to a certain distension of the middle cheek portions of the patient. This is important not only for keeping the effective mouth opening wide, but also for compensating for "hollow cheeks" which, seen from the outside, may present difficulties as far as the sealing of an anaestesia mask against the skin is concerned. For this reason the mouthpiece is highly advantageous even when the patient has no upper teeth left.

In the mounted position as shown in FIG. 2 the resiliency of the bent loop member 6 will serve to constantly urge the upper and lower mouthpiece portions away from each other and thus with a reasonable force ensure a totally safe holding of the mouthpiece in its desired position. The patient may even close the mouth temporarily.

FIG. 2 further shows the modification that the loop member 6 is made of a plastic tube or hose piece of the required resiliency, secured by insertion over respective connector pin portions 8 projecting rearwardly from the outer ends of the stubs 4. Though it has been found that an integral loop member 6 as shown in FIG. 1 may suit a very high percentage of the patients, it may nevertheless be advantageous to enable the loop to be individually length adjusted, and this will be true for the embodiment as shown in FIG. 2. An adjustment of the loop in FIG. 1 may be obtained by cutting the loop and connecting the cut ends by a piece of a plastic or rubber hose.

The connector pins 8 may be of such a flattened cross sectional shape that the hose ends are deformed to decrease their width in the horizontal cross direction and increase their thickness in the vertical plane, whereby it is counteracted that sharp hose bends occur just behind the ends of the connector pins; such bends would adversely affact the general resiliency between the upper and lower mouthpiece portions.

The position of the stubs 4 as spaced from the rear ends of the tray member 2 is advantageous both for obtaining a safe holding force on the entire tray member under all conditions of use, for distending the cheeks, and for enabling the required resiliency to be produced over a relatively long length of the loop material, even assisted by resilient twisting of the stubs 4, whereby the actual spring force as felt by the patient is almost the same reasonably low force no matter how much the mouth is opened or closed. Principially, of course, nothing will prevent that the loop member could be joined to the tray member immediately at the rear ends thereof, and if hereby the spring action has to be concentrated in a relatively narrow area it may be preferable to produce the mouthpiece with the loop in its natural position extending downwardly from the tray member ends, e.g. in a plane perpendicular to the general plane of the tray member. It will be appreciated, however, that such a mouthpiece could hardly be advantageous over the embodiments shown in the drawing.

What is claimed is:

1. A mouthpiece for protecting the upper dentition of patients during medical or surgical work involving oral intervention, comprising an arched tray element mountable so as to cover at least a major portion of the outside of the upper row of teeth, the lower end of the teeth and at least the lower portion of the inside of the teeth, fastening means being provided for removably holding the tray element in engagement with the upper tooth row, characterized in that the fastening means are constituted by a resilient rod or tube loop member interconnecting the opposed rear portions of the arched tray element so as to be resiliently downwardly and forwardly bendable about a generally transverse axis area in order to hereby be positionable with its originally rearmost arched portion located bottomwise in the groove between the front or outer side of the lower dentition and the inner side of the underlip of the patient to thereby exert a downwardly directed resilient pressure, the counter pressure of which will serve to maintain the arched tray element in engagement with the upper dentition of the patient.

2. A mouthpiece according to claim 1, characterized in that the opposed ends of the resilient rod or tube loop member are connected to the rear portions of the arched tray element adjacent the outsides thereof in some distance in front of their rear ends, and that the loop member end portions just behind the connection areas project rearwardly and outwardly before they start converging towards each other in a transverse area spaced behind the rear ends of the arched tray element.

3. A mouthpiece according to claim 1 or 2, characterized in that the loop member end portions are connected to the opposed outsides of the arched tray element through a resiliently twistable stub projecting substantially perpendicularly from the respective outside of the tray element.

4. A mouthpiece according to claim 1 or 2 characterized in that the loop member is a resilient tube which is endwise insertable onto opposed connector stubs projecting rearwardly from the outer ends of respective protrusions on the opposed outsides of the arched tray element.

5. A mouthpiece according to claim 3, characterized in that the loop member is a resilient tube which is endwise insertable onto opposed connector stubs projecting rearwardly from the outer ends of respective protrusions on the opposed outsides of the arched tray element.

* * * * *